United States Patent [19]
Cappelletti et al.

[11] Patent Number: 5,998,162
[45] Date of Patent: Dec. 7, 1999

[54] PRODUCTION OF SECONDARY METABOLITES WITH PLANT CELLS IMMOBILIZED IN A POROUS INORGANIC SUPPORT

[75] Inventors: Elsa Mariella Cappelletti, Padua; Giovanni Carturan, Albignasego; Anna Piovan, Padua, all of Italy

[73] Assignee: Biosil AG, Italy

[21] Appl. No.: 08/952,104

[22] PCT Filed: May 18, 1995

[86] PCT No.: PCT/IT95/00083

§ 371 Date: Nov. 17, 1997

§ 102(e) Date: Nov. 17, 1997

[87] PCT Pub. No.: WO96/36703

PCT Pub. Date: Nov. 21, 1996

[51] Int. Cl.[6] .............. C12P 1/00; C12N 11/14; C12N 5/00; C12N 5/04
[52] U.S. Cl. ............ 435/41; 435/176; 435/395; 435/402; 435/410; 435/289.1
[58] Field of Search .................. 435/41, 395, 399, 435/402, 289.1, 174, 176, 177, 410

[56] References Cited

U.S. PATENT DOCUMENTS

| | | | |
|---|---|---|---|
| 4,845,054 | 7/1989 | Mitchener | 437/238 |
| 5,041,138 | 8/1991 | Vacanti et al. | 623/16 |

FOREIGN PATENT DOCUMENTS

| | | |
|---|---|---|
| 0 267 470 | 10/1987 | European Pat. Off. . |
| 2 185 998 | 1/1986 | United Kingdom . |

OTHER PUBLICATIONS

*Journal of Biotechnology*, 30 (1993) 197–210.

*Primary Examiner*—David M. Naff
*Attorney, Agent, or Firm*—Henry D. Coleman; R. Neil Sudol

[57] ABSTRACT

Secondary metabolites of viable plant cells are produced with the cells immobilized in a porous inorganic support. Immobilization includes the steps of: (a) preparing a support comprising a substantially uniform and porous matrix of inorganic material having a tensile strength of at least 500 MPa; (b) introducing a culture of viable plant cells into the pores of said matrix; (c) entrapping the plant cells by coating the matrix with a sol or colloidal suspension not interfering with the cell viability; and (d) immobilizing the entrapped cells within the matrix with a reactive gas including a carrier gas saturated with volatile $SiO_2$ or organic modified $SiO_2$ precursors. The tensile strength may be provided by impregnating the matrix with a gelling solution of $SiO_2$ precursor for increasing stiffness of the matrix. The matrix may be a $SiO_2$ or inorganic oxide matrices, in which the weight ratio between cell load and inorganic matrix ranges between $1\times10^{-4}$ and $1\times10^{-2}$. The immobilized cells are not released in solution over a period of 6 months and maintain their viability while producing secondary metabolites.

14 Claims, 3 Drawing Sheets

PRODUCTION OF SECONDARY METABOLITES WITH PLANT CELLS IMMOBILIZED IN A POROUS INORGANIC SUPPORT

The application is a 371 of PCT/IT95/00083, filed May 18, 1995.

FIELD OF THE INVENTION

The present invention relates to a process for continuously or discontinuously producing secondary metabolites of viable plant cells in porous and inorganic matrices.

The invention further relates to an article suitable for entrapping and immobilizing the plant cells in such a condition to maintain their viability for production of secondary metabolites.

The production of secondary metabolites on an industrial scale constitutes the main but not the only field of application of the present invention, since the process according to the invention and the immobilization obtained, as described in detail hereafter, can be advantageously used in any other equivalent field in which immobilized plant cells are used.

BACKGROUND OF THE INVENTION

The most commonly used immobilization matrix is algal polysaccharide alginate, cross-linked with calcium ions as described in FEBS Lett. 103: 93–97 (1979) and 122: 312–316 (1980), Plant Cell Rep. 5: 302–305 (1986), and Appl. Microbiol. Biotechnol. 30: 475–481 (1989). Other methods include entrapment with polyurethane foam, described in Biotechnol. Bioeng. 33: 293–299 (1989), 35: 660–667 (1990), Appl. Microbiol. Biotechnol. 33: 36–42 (1990), 37: 397–403 (1991) and 35: 382–392 (1991).

The use of porous and amorphous sol-gel derived silica for entrapment of viable cells has been described in cases of non-plant cells, reported in J. Biotechnol. 30: 197 (1993), J. Ceram. Soc. Jpn. 100: 426 (1992), Biochim. Biophys. Acta 276: 323 (1972), Chemistry of Materials 6: 1605–1613 (1994) and Angew, Chem, Int. Engl. 34: 301–303 (1995). These latter cannot be considered as methods actually suitable for applications to higher plant cells, which are severely poisoned under the experimental conditions reported for immobilization of bacteria and yeast cells. As for processes applied to, and claimed for, plant cell immobilization, they entail some problems: first of all, processes based on simple adhesion to the surface cannot properly be considered as immobilization, since cell reproduction and the increase in biological mass unavoidably cause release of cells in solution.

Polyurethane foaming matrices may cause severe transport limitations to and from immobilized cells. One important drawback of these host matrices is their poor mechanical stiffness, so that prolonged use for industrial production in practice does not appear feasible.

Immobilization in alginate beads allows direct contact of cells with the gel matrix, so that the cells are inevitably subjected to a high concentration of a variety of ions and organic compounds, causing negative physiological effects.

SUMMARY OF THE INVENTION

A main object of the present invention is therefore to overcome the above described disadvantages by means of a process which allows plant cells to be immobilized while maintaining their viability and avoiding the release of cells from the matrices, with free transport between the immobilized phase and the culture medium.

A further object of the present invention is to provide a process which may be repeated in standard conditions with constant results.

Another object of the invention is to provide a host matrix with stiffness suitable to tolerate stress and share strain during production.

Still another object is to provide immobilization articles or matrices which, allowing free exchange of organic species and nutrients through the open pores, ensure increased intercellular contacts and consequently the potential for biochemical communications.

A further object of the invention is to provide a process which may be performed with industrial-scale devices and relevant production equipment.

These objects are achieved by a process comprising the steps of:

(a) providing a support comprising a substantially uniform and porous matrix of inorganic material having a tensile strength of at least 500 MPa;

(b) introducing a culture of viable plant cells into the pores of said matrix;

(c) entrapping the plant cells by coating the matrix with a sol or colloidal suspension not interfering with the cell viability;

(d) immobilizing the entrapped cells within the matrix with a reactive gas including a carrier gas saturated with volatile $SiO_2$ or organic modified $SiO_2$ precursors.

The employment of culture systems in which plant cells are immobilized on an inert support is now recognized as a means by which the environment of the cells can be manipulated simply and the yields of specific secondary metabolites increased over those of liquid-suspended cells, thus allowing continuous production thereof.

The immobilization of plant cells obtained according to the invention covers a vast range of applications for the production of secondary metabolites, since the process is not limited to a single plant species and the coupling between the mechanical stiffness of the matrices with the porosity of deposited precursor-derived silica allows the application of this immobilized biosystem to heterogeneous phase production for large-scale industrial bioreactors.

The applicant has now surprisingly found—and this is one main aspect of the present invention—that it is possible to obtain immobilization of plant cells with maintenance of their viability.

DETAILED DESCRIPTION OF THE INVENTION

Figure 1:
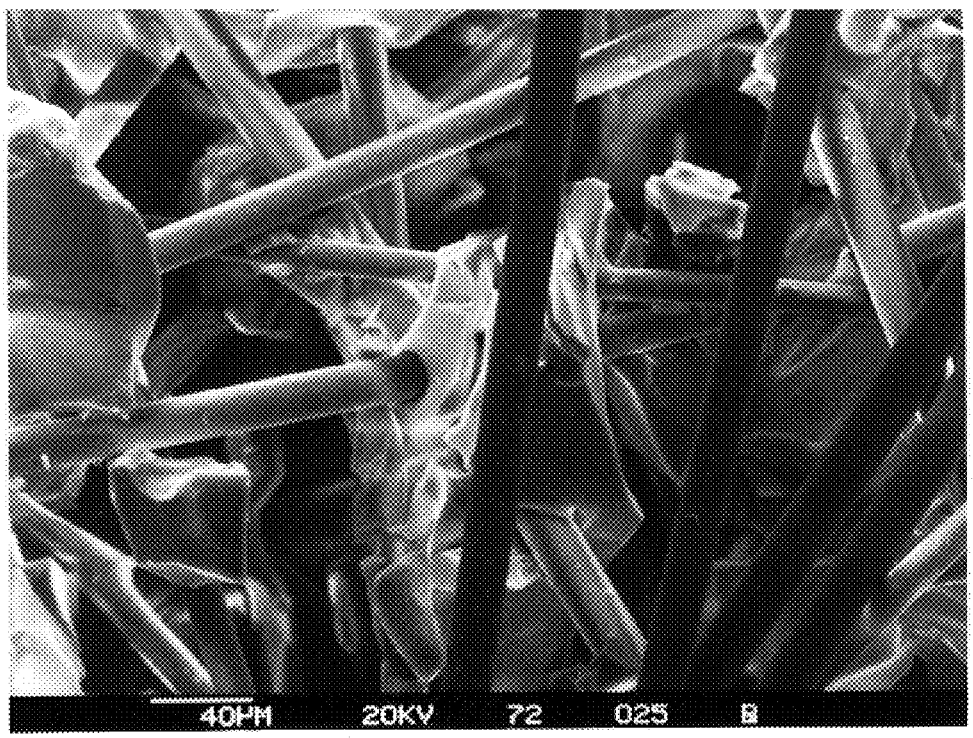
FIG. 1 is a photomicrograph of a glass fiber fabric, according to the invention, after coating and stabilization according to step (a)

The matrix may be a glass fiber fabric, a porous glass, ceramic, clay or similar inorganic material.

More preferably, the matrix may be a fabric or an agglomerate of inorganic fibres, which is impregnated with a gelling solution of $SiO_2$ precursors or similar materials to increase the stiffness thereof. For example, an ordinary glass fabric may be used having a fiber density between 100 and 700 mg/cm², which fabric is dipped in a gelling solution of $Si(OEt)_4$ and $CH_3SiH(OEt)_2$. The wet material is set aside for 15 days, developing a surface deposit of amorphous silica. The stiff fabric thus obtained may be cut into pieces of variable geometry.

In general, the glass fabric is preferably composed of fibers between 30 and 10 μm in diameter, with variable composition of the glass phase. The texture is compatible with the introduction of plant cells according to step (b). The concentration of $Si(OEt)_4$ and $CH_3SiH(OEt)_2$ used to increase the stiffness and mechanical stress of the fibre matrix ranges between 10 and 100 g/dm³ of nominal $SiO_2$. The solvent is preferably chosen among one or more of the following: ethanol, methanol, butanol, acetone, tetrahydrofuran, dimethylformamide. The solution contains a $H_2O$ concentration ensuring hydrolysis of Si—OR groups, and is acidified with a nominal $H^+$ concentration ranging between $1 \times 10^{-1}$ and $1 \times 10^{-5}$ M. The viscosity suitable for step (a) preferably ranges between 0.2 and 100 Pas. The operation conducted with gelling solutions of species $Si(OR)_4$, $SiH_x(OR)_{4-x}$ and $SiX_x(OR)_{4-x}$ where x=1,2; R=alkyl or aryl, X=halide or alkyl, leads to the same results. Prepolymerized silicon derivatives of these species produce identical results.

Pieces of glass fabric with identical geometries may be assembled in a pile to become self-carrying after step (a).

The introduction of cells in accordance with step (b) is performed by simply shaking glass fabric pieces into the viable cell suspension. The same result may be obtained by filtering the suspension across the glass fabric, mounted on a suitable support.

Treatment with colloidal $SiO_2$-sol suspension, leading to primary entrapment of the cells in the voids of the glass fabric in accordance with step (c), is carried out with a colloidal $SiO_2$ suspension buffered at pH 4.0–6.5. This operation, conducted with sol suspension of aluminum hydroxide or other hydrated oxides, gives place to the same results. Different extraction rates, mentioned in step (c), are required owing to the different fiber density of the fabric; the highest rates are used for materials with lowest fiber densities. The amount of hydroxide or hydrated oxide dispersed in the sol or colloidal suspension ranges from 5 to 200 g/dm³, and the colloidal particles may have a diameter comprised between 10 and 1000 nm.

Consolidation of the cell entrapment is performed by step (d). The choice of $Si(OR)_4$, $SiH_x(OR)_{4-x}$ and/or $SiX_x(OR)_{4-x}$, influences the adhesion of the $SiO_2$-like deposit, its stiffness and bulk porosity. The process is carried out in the gas phase anchoring silicon oxide species to hydroxide groups on the cell surface and the glass fabric. The solution or mixture of $Si(OR)_4$, $SiH_x(OR)_{4-x}$ and/or $SiX_x(OR)_{4-x}$ displays variable concentrations of components ranging among molar ratios $Si(OR)_4/SiH_x(OR)_{4-x}$ from 0.1/1 and 1/0.01, molar ratios $SiH_x(OR)_{4-x}/SiX_x(OR)_{4-x}$ from 0.01/2 and 1/0.1, molar ratios $Si(OR)_4/SiX_x(OR)_{4-x}$ from 1/0.01 and 0.01/1. The chemical species $SiHR(OR)_2$ where R is an alkyl or aryl, is also used in solutions or mixtures with $Si(OR)_4$ using ratios $SiHR(OR)_2/Si(OR)_4$ between 0.01/2 and 1/0.03.

The solutions or mixtures of these components are used to achieve suitable vapor pressure in the carrier gas flow. These solutions or mixtures are kept at constant temperature, variable between 20° C. and 120° C., in a thermostated oil bath. The carrier gases used in this invention are air, nitrogen, argon or helium. The total flow of the gas is preferably comprised between 0.2 and 80 cm³/minute per square centimeter of the geometrical surface of glass fabric. Treatment with vapor-phase water is carried out in a current of inert gas by bubbling the gas into distilled water thermostated between 10 and 70° C.; the total flow ranges between 0.01 and 10 cm³/minute per cm² of the geometrical surface of the glass fabric.

Further characteristics and advantages of the invention will become apparent from the description of two examples, illustrated hereafter only by way of non-limitative examples with reference to the accompanying drawings.

EXAMPLE 1

An ordinary fabric of glass fibers, textured by 25×25 μm meshes, was cut into disks of about 25 mm diameter. These were hydrolysed by fluxing steam for 2 hours. A 1/1 $Si(OEt)_4$/$CH_3SiH(OEt)_2$ ethanol solution with nominal $SiO_2$ concentration=100 g/dm³ was hydrolysed with stoichiometric $H_2O$, $OR/H_2O$=0.5 molar ratio, and set aside until achievement of viscosity=100 Pas.

The disks dipped into the solution were extracted at a rate of 1 mm/s. These materials, consolidated over 15 days at 40° C., show that the glass fibers are coated by a deposit of amorphous and porous $SiO_2$-like material still holding Si—H and Si—$CH_3$ moieties. The morphology of the coated fabric is shown by the SEM micrograph of FIG. 1.

Figure 2:
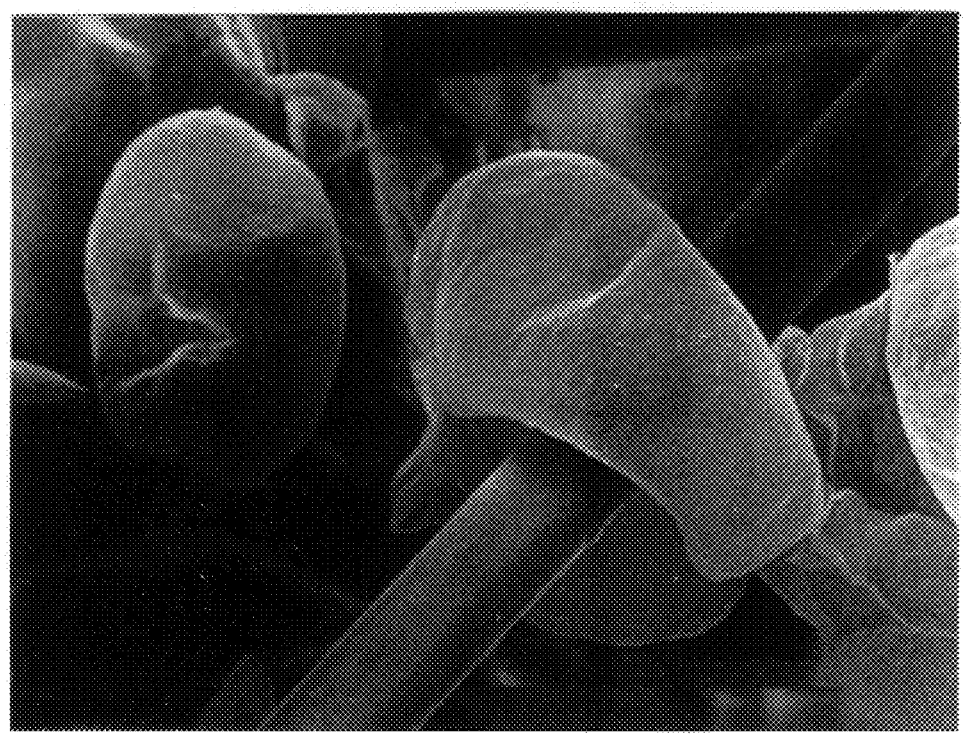
FIG. 2 is a photomicrograph of cells in the fabric according to step (b)

A cell suspension culture of Coronilla vaginalis L. (cell line 39 RAR generated from the leaf in 1991), was kept in Gamborg's basal growth $B_5$ medium supplemented with 3% (w/v) of sucrose, 1.3 mg/l of 2,4-dichlorophenoxyacetic acid, 0.25 mg/l of kinetin and 0.25 mg/l of naphthalenacetic acid. The pH was adjusted to 5.7 before sterilization. Cells were transferred to fresh medium at intervals of 2 weeks and maintained at 25° C on a gyratory shaker (110 rpm) in a 12-hour photoperiod. This cell suspension was used to soak the sterile disks; the operation was performed under sterile conditions, leaving the single disks in Petri dishes filled with the cell culture for 3 days on a rotary shaker at 90 rpm, at 25° C., with a 12-hour photoperiod. Cells trapped in the fabric were observed by SEM, as shown in FIG. 2.

Single disks were washed on the surface, to eliminate any non-trapped cell load. The disks were dipped into a $SiO_2$ sterile sol suspension. This colloidal suspension, with a particle diameter of 40 nm, was buffered at pH 5.7 with phosphatic alkaline salts and diluted with distilled water to a nominal $SiO_2$ concentration of 20 g/dm³.

Figure 3:
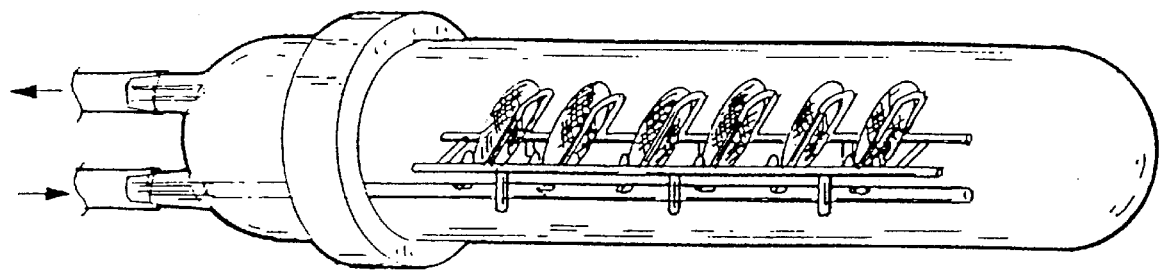
FIG. 3 is a drawing of the glass reactor used in step (d)
Figure 4:
FIG. 4 is a photomicrograph of cells immobilized in the fabric, according to step (d).

The disks, extracted at a rate of 1 mm s$^{-1}$, were mounted on a rack and introduced into the glass reactor depicted in FIG. 3. This reactor was supplied with a gas flow of air saturated by $Si(OEt)_4$ and $CH_3SiH(OEt)_2$ from a 80/20 molar ratio solution thermostated at 85° C. Total gas flow was 15 ml minute$^{-1}$ per 125 cm² of the geometrical surface of the disks. Treatment was continued for 3 minutes; then, using the same total gas flow, disks were treated for 2 minutes with air saturated with steam by bubbling into water thermostated at 70° C. Cells in the glass fiber disk were observed by SEM, and appeared to be immobilized by the $SiO_2$-like deposit, as shown in FIG. 4. Single disks were kept in $B_5$ medium without hormones, at 25° C. in a 12-hour photoperiod on a rotary shaker.

The retained viability of cells was determined by property of plant mitochondria to reduce tetrazolium salt (TTC), affording red formazan, easily detectable by absorption spectroscopy at 485 nm. TTC (0.5% w/v) was dissolved in sodium phosphate buffer at pH 7. The TTC solution was added to single disks and incubated without shaking for 24 hours in the dark at 23° C. The red formazan was extracted from the immobilized cells with 5 ml of 95% ethanol for 15 minutes. Cell viability was also tested by cultivating two stretched disks on solid $B_5$ medium supplemented with growth hormones. The induction of microcalli was used as indicator of cell culture viability.

Maintenance of immobilization was tested by controlling the occurrence of free cells in the medium of 10 disks kept at 25° C. in a 12-hour photoperiod on a rotary shaker. Tests were performed every 14 days by direct microscopic observation of the solution or after 21 days' ageing of the solution supplemented with hormones.

Contamination of the solution by immobilized cells over a period of six months was checked and found to be nil.

Immobilized cells produce secondary metabolites, as coumarin compounds, since fluorescence analysis of the medium, where immobilized cells are maintained, indicates the presence of fluorescent compounds, the concentration of which increases over four months of observation.

EXAMPLE 2

Cell suspension culture of Coronilla viminalis Salisb. (cell line 7 CFP generated from the leaf in 1991) was kept in MS medium supplemented with 3% (w/v) of sucrose, 1.3 mg/l of 2,4-dichlorophenoxyacetic acid, 0.25 mg/l of kinetin and 0.25 mg/l of naphthalenacetic acid. The pH was adjusted to 5.7 before sterilization.

Cells were transferred to fresh medium at intervals of 2 weeks and maintained at 25° C. on a gyratory shaker (110 rpm) in a 12-hour photoperiod. This cell suspension was used to soak the sterile disks obtained according to the method used in example 1.

Cells were trapped and immobilized according to the method used in example 1. Single disks are maintained in MS medium without hormones, at 25° C. in a 12-hour photoperiod on a rotary shaker.

Cells viability was tested by TTC reduction and by microcallus induction from stretched disks on solid MS medium supplemented with growth hormones.

No cell release from disks into the medium was observed over a period of six months.

We claim:

1. An article for maintaining a culture of viable plant cells in a stationary phase for in situ applications for the production of secondary metabolites, said article comprising a support made of at least one element comprising a porous matrix of inorganic material selected from the group consisting of porous glass, porous ceramic, porous inorganic fabric and porous agglomeration of glass fibres having a substantially uniform distribution of pores for entrapping the cells and maintaining them in a viable condition, wherein said matrix has an overall ultimate tensile strength of at least 500 MPa which has been provided by impregnating said matrix with a gelling solution of $SiO_2$ precursor for increasing stiffness of said matrix, said element being arranged within a closed reactor supplied with a flow of a reactive gas including a carrier gas saturated with volatile $SiO_2$ or organically modified $SiO_2$ precursors for immobilizing the viable plant cells and for production of the secondary metabolites thereof.

2. The article as claimed in claim 1, wherein the porous matrix incorporates stimulating means comprising basal grow-media supplemented by sugars, organic acids and enzymes suitable for preserving or enhancing the physiological functions of the plant cells.

3. The article according to claim 1 wherein said support element is disk shaped.

4. A process for the production of secondary metabolites of viable plant cells, comprising the steps of:

(a) providing a porous inorganic support comprising a uniform and porous matrix of inorganic material, said matrix having an overall tensile strength of at least 500 MPa;

(b) introducing a suspension of viable plant cells into the pores of said matrix;

(c) coating the matrix in which the plant cells have been introduced with a sol or colloidal suspension selected so as to maintain cell viability and to provide entrapped plant cells within the matrix;

(d) in a closed reactor immobilizing the entrapped plant cells within the matrix with a reactive gas including a carrier gas saturated with volatile $SiO_2$ or organically modified $SiO_2$ precursors;

(e) feeding the immobilized cells with nutrients and growth media to promote the production of said secondary metabolites; and (f) collecting the secondary metbolites produced by the immobilized plant cells.

5. A process as claimed in claim 4, wherein the carrier gas used in the immobilization step d) is saturated with $Si(OR)_4$, $SiH_x(OR)_{4-x}$ and/or $SiX_x(OR)_{4-x}$, wherein X=1 or 2, R is an alkyl group or an aryl group and X is a halide or an alkyl group.

6. A process as claimed in claim 4, wherein the immobilized cells from step (d) are treated with water in a vapor-phase.

7. A process as claimed in claim 4, wherein the plant cells are generated from tissues of plants maintained under chemical and physiological conditions in growth media ensuring cell viability and production of secondary metabolites.

8. A process as claimed in claim 4, wherein the introducing step (b) comprises physical methods including shaking the porous inorganic support into the cell suspension or filtering the cell suspension across the porous inorganic support.

9. A process as claimed in claim 4, wherein said immobilizing in step d) with reactive gas is carried out in a current of inert gas as the carrier gas at substantially constant temperature and flow rate to prevent the cells from being released during production of secondary metabolites.

10. A process as claimed in claim 4, wherein stimulating means comprising basal growth-media supplemented by sugars, organic acids and enzymes is added to the immobilized cells immediately after the immobilization step (d) to increase the production of secondary metabolites and enhance the physiological functions of the plant cells.

11. A process as claimed in claim 4, wherein the matrix forming said porous inorganic support is made of porous glass, ceramic or clay.

12. A process as claimed in claim 4, wherein the matrix forming said porous inorganic support is a porous inorganic fabric or an agglomeration of inorganic fibres.

13. A process as claimed in claim 4, where the sol or colloidal suspension is an aqueous suspension of inorganic oxides which includes colloidal particles, having a pH ranging from 4.0 to 6.5 and a viscosity between 0.2 and 100 Pas.

14. A process as claimed in claim 13 wherein said inorganic oxide is aluminum hydroxide or $SiO_2$, the amount of said aluminum hydroxide or $SiO_2$ dispersed in the sol or colloidal suspension ranges from 5 to 200 g/dm$^3$, and said colloidal particles have a diameter between 10 and 1000 nm.

* * * * *

UNITED STATES PATENT AND TRADEMARK OFFICE
CERTIFICATE OF CORRECTION

PATENT NO. : 5,998,162
DATED : December 7, 1999
INVENTOR(S) : Cappelletti et al.

It is certified that error appears in the above-identified patent and that said Letters Patent is hereby corrected as shown below:

On the first page of the patent, the Assignee's residence should be changed to Liechtenstein.

Signed and Sealed this

Tenth Day of April, 2001

Attest:

NICHOLAS P. GODICI

Attesting Officer          Acting Director of the United States Patent and Trademark Office